March 12, 1940. J. S. ELLIOTT Plant Pat. 369
ROSE PLANT
Filed July 12, 1939
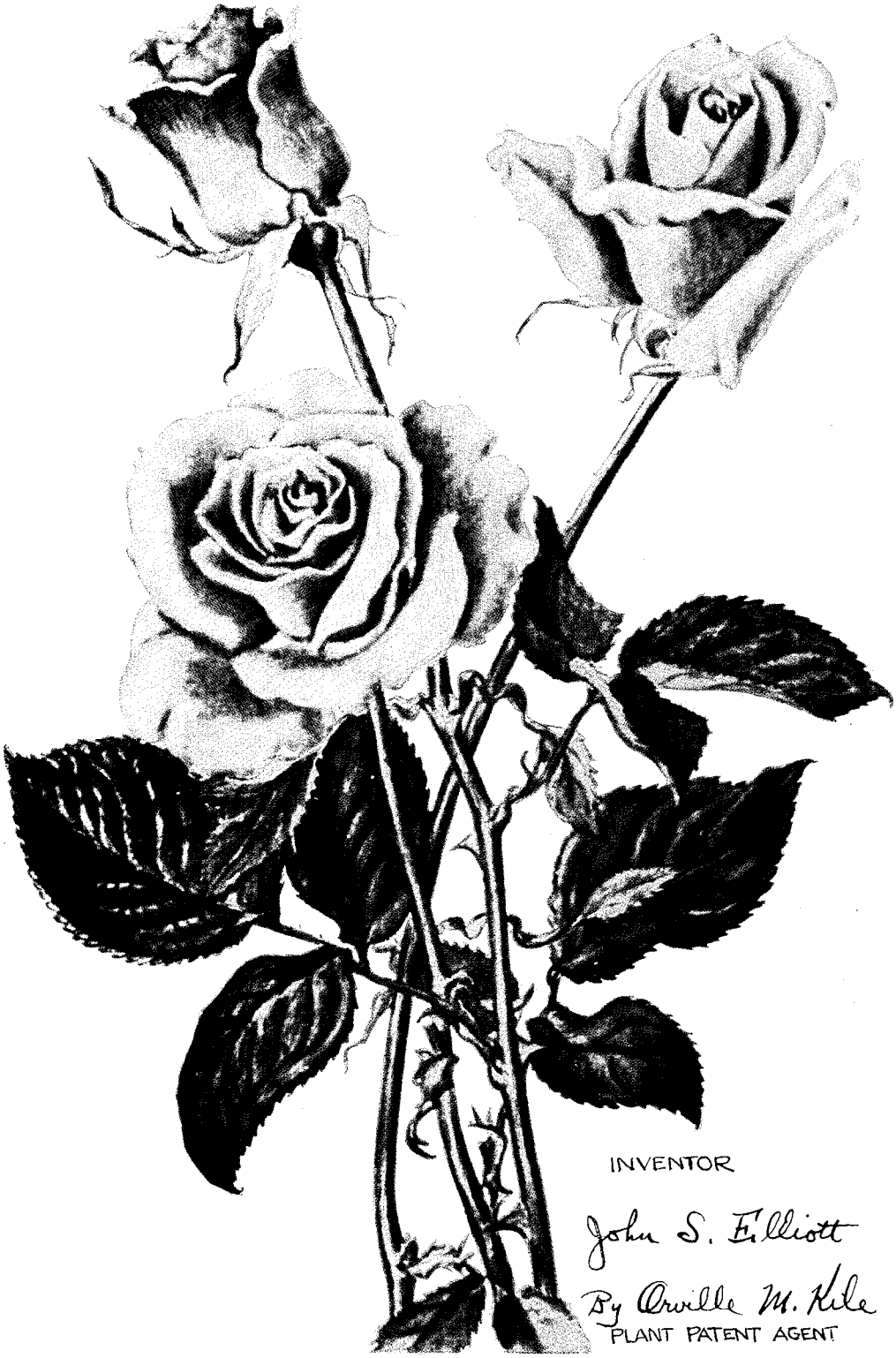
INVENTOR
John S. Elliott
By Orville M. Kile
PLANT PATENT AGENT Patented Mar. 12, 1940

Plant Pat. 369

UNITED STATES PATENT OFFICE

369

ROSE PLANT

John S. Elliott, Dover, N. H.

Application July 12, 1939, Serial No. 284,115

1 Claim. (Cl. 47—61)

My new discovery relates to improvements in hybrid tea roses and is a sport of Vierlander discovered by me in one of my greenhouses. This sport was actually found growing on and from a Vierlander rose plant. Improvement pertains particularly to difference in color of its blossoms as compared to those of its parent, the blossoms being rose red whereas the blossoms of Vierlander are salmon pink. The growth habits of my new variety are similar to those of its parent.

The original illustration accompanying this application shows a bud, a partly opened flower and a fully opened flower of this new variety in approximately their true colors. It must be understood, however, that the artist cannot show the full brilliance and velvety appearance which is apparent in the natural flower.

The new variety has been asexually reproduced, and its characteristics have been definitely established.

Following is a detailed description of my new variety, color designations referring to Ridgway's Color Standards and Nomenclature except where the usual dictionary term is obviously intended.

*The plant*

Growth:

Upright bush. Very strong and vigorous. Wood hard. Very prolific.

*Stems.*—Long and exceedingly stiff and strong.

*Color.*—Kronberg's Green (Plate XXXI).

*Thorns.*—Numerous long pinkish white thorns are found in irregular position on stems. They are downward-pointing, very sharp, and have a narrow base. Sharp prickles occur on under side of rachis. A few small spines occur on the peduncle.

*New shoots.*—Smooth; Medal Bronze to Dark Citrine (Plate IV).

Foliage:

Abundant; healthy; unusually attractive.

*Leaves.*—Compound, 3 to 5 leaflets. First leaf usually small and irregular in shape.

Leaflets:

*Size.*—Large. Terminal leaflets usually measure 2½ to 2¾ inches long by 1½ 1⅝ inches wide. Lateral leaflets smaller.

*Shape.*—Elliptical with acuminate apex.

*Color.*—Yew Green (Plate XXXI) edged with reddish purple which is approximately Indian Lake (Plate XXVI). New foliage is Deep Brownish Vinaceous (Plate XXXIX) to Deep Hellebore Red (Plate XXXVIII) on under surface. Upper surface is Yellowish Olive (Plate XXX) edged with Indian Lake (Plate XXVI).

*Texture.*—Smooth; leathery but not particularly heavy.

*Aspect.*—Soft; dull on upper surface. Veins much more prominent on under side than upper side. Has appearance of soft dull kid leather.

*Serrations.*—Fine; sharp; single; even.

*Rachis.*—Heavy. Upper side grooved; purple tinted. Under side has several sharp spines.

*Stipules.*—Wide; long; wavy; clinging except for sharp points which sometimes recurve toward stems.

Disease resistance:

Very resistant to diseases common to roses.

Blooming habit:

Abundant; intermittent; flowers borne singly.

*The flower*

Bud:

*Size.*—Large.

*Form.*—At first long pointed, opening to urnshape.

*Color.*—The nearest approach in Ridgway's Color Standards is Rose Red (Plate XII) but the bud color is slightly deeper and much more brilliant than shown by the plate. The color is almost uniformly distributed with no light area at the base.

*Sepals.*—Mostly simple; curl backward as bud opens.

*Peduncle.*—Long and stiff, holding blooms erect; lighter green than the stems, being approximately Parrot Green (Plate XXXI); has numerous fine spines.

*Opening.*—Opens evenly and slowly.

Bloom:

*Size.*—Large, attaining a spread of 4½ to 5 inches when fully expanded.

*Form.*—High-centered. The outer petals are large and extend above the center petals, giving the top of the opening flower a squared or depressed appearance in the center. The outer petals turn backward slightly at the edges in a very attractive manner, but the form of the rose is retained throughout its life.

*Petalage.*—The usual number of petals in the month of May is from 22 to 25.

Petals:

*Color.*—The bud lightens slightly as it opens until it becomes a brilliant Rose Red (Plate XII) in the half-opened flower. As the flower opens further the color changes to a pure Tyrian Rose (Plate XII)—in all of its stages having a much greater brilliance than is shown in the color plates. The color is almost uniformly distributed over the petals except that frequently a white vertical streak is visible on the petals. Color changes very little after the rose is fully opened.

*Size.*—Outer petals very large, measuring about 2 inches vertically and 2 to 2¼ inches laterally.

*Shape.*—Round; cupped; edges smooth.

*Texture.*—Heavy.

*Appearance.*—Inside surface velvety; outside surface satiny.

*Fragrance.*—Moderate; pleasing.

*Lasting quality.*—Exceptionally good as a cut flower.

*Persistence.*—Petals cling until flower is old.

*Reproductive organs*

Pistils:

Many; bunched; enclosed by pithy ring.

*Styles.*—Uneven lengths; short; Carmine (Plate I).

*Stigmas.*—Carmine, tipped with very small dot of yellowish white.

Stamens:

Many; arranged in circle around the pithy ring which separates them from the pistils.

*Filaments.*—Dark Vinaceous (Plate XXVII); uneven lengths; anthers borne by most of them.

*Anthers.*—Large; Deep Vinaceous (Plate XXVII) in center, edged by a shade which is approximately Ochraceous-Buff (Plate XVI).

Ovaries:

Partially protruding from calyx.

Hips:

Slender.

*Comparison*

The variety of red rose known to me which is most like my new variety is the subject of Plant Patent No. 323. However, it differs in the following important respects.

My variety is a sport of Vierlander and has its parent's same strong and vigorous growth, while No. 323 is a sport of Better Times.

The bud of my new variety is longer than that of No. 323.

Although both varieties are red roses their color is in entirely different ranges. My new rose is Rose Red which later turns to Tyrian Rose. The color of No. 323 is described as being between Carmine and Pomegranate Purple, and the general tonality given as Carmine.

The sepals of the flower of my new variety are much more simple than those of No. 323 which are long and serrated.

The petals of my new variety are less fluted than those of No. 323.

Having thus disclosed my discovery, I claim:

A new and useful variety of hybrid tea rose plant with qualities in combination substantially as shown and described, characterized particularly by its unusually attractive soft foliage; its very strong and heavy stems; and its large fragrant flowers of high-centered form which is retained, and brilliant velvety color approximately uniform Rose Red which later changes to Tyrian Rose.

JOHN S. ELLIOTT.